United States Patent
Li

(10) Patent No.: US 11,547,505 B2
(45) Date of Patent: Jan. 10, 2023

(54) METHOD FOR CONTROLLING A MECHANICAL ARM OF A SURGICAL ROBOT FOLLOWING THE MOVEMENT OF A SURGICAL BED AND A DEVICE THEREFOR

(71) Applicant: CHENGDU BORNS MEDICAL ROBOTICS INC., Sichuan (CN)

(72) Inventor: Zhiqiang Li, Sichuan (CN)

(73) Assignee: CHENGDU BORNS MEDICAL ROBOTICS INC., Sichuan (CN)

( * ) Notice: Subject to any disclaimer, the term of this patent is extended or adjusted under 35 U.S.C. 154(b) by 0 days.

(21) Appl. No.: 17/509,489

(22) Filed: Oct. 25, 2021

(65) Prior Publication Data

US 2022/0125537 A1 Apr. 28, 2022

(30) Foreign Application Priority Data

Oct. 23, 2020 (CN) .......................... 202011150378.1

(51) Int. Cl.
*A61B 34/37* (2016.01)
*A61B 34/20* (2016.01)
(Continued)

(52) U.S. Cl.
CPC .............. *A61B 34/37* (2016.02); *A61B 34/20* (2016.02); *G16H 20/40* (2018.01); *A61B 2034/2055* (2016.02); *A61B 2034/301* (2016.02)

(58) Field of Classification Search
CPC combination set(s) only.
See application file for complete search history.

(56) References Cited

U.S. PATENT DOCUMENTS 7,822,466 B2 10/2010 Stoianovici et al.
9,259,282 B2 2/2016 Blohm et al.
(Continued)

FOREIGN PATENT DOCUMENTS

CN 203752148 U 8/2014
CN 105816243 A 8/2016
(Continued)

OTHER PUBLICATIONS

International Search Report (Translation) for International Patent Application No. PCT/CN2018/097541; dated Dec. 18, 2018; 2 pages.
(Continued)

*Primary Examiner* — Scott Luan
(74) *Attorney, Agent, or Firm* — Ulmer & Berne LLP

(57) ABSTRACT

A method includes: synchronously calculating offsets of a first mechanical arm, a second mechanical arm and an endoscopy mechanical arm corresponding to a change of posture of the surgical bed when the change of posture of the surgical bed is detected in real time; calculating target joint readings of each of the first mechanical arm, the second mechanical arm and the endoscopy mechanical arm based on the offsets; adjusting in real time the first mechanical arm, the second mechanical arm and the endoscopy mechanical arm, based on the calculated target joint readings. The method acquires the joint readings of the mechanical arm of the surgical robot with information about a change of posture of the surgical bed so as to achieve the purpose of synchronizing the mechanical arm with the change of posture of the surgical bed.

13 Claims, 7 Drawing Sheets

(51) Int. Cl.
*G16H 20/40* (2018.01)
*A61B 34/30* (2016.01)

(56) References Cited

U.S. PATENT DOCUMENTS

| | | | |
|---|---|---|---|
| 10,993,776 | B2 | 5/2021 | Li |
| 2002/0082612 | A1 | 6/2002 | Moll et al. |
| 2007/0089557 | A1 | 4/2007 | Solomon et al. |
| 2007/0156285 | A1 | 7/2007 | Sillman et al. |
| 2010/0069920 | A1 | 3/2010 | Naylor et al. |
| 2010/0204713 | A1 | 8/2010 | Ruiz Morales |
| 2010/0225209 | A1 | 9/2010 | Goldberg et al. |
| 2011/0277776 | A1 | 11/2011 | Mcgrogan et al. |
| 2013/0085389 | A1 | 4/2013 | Tsang et al. |
| 2013/0085510 | A1* | 4/2013 | Stefanchik ............. A61B 34/30 901/30 |
| 2016/0001038 | A1 | 1/2016 | Romo et al. |
| 2016/0030115 | A1* | 2/2016 | Shen .................. A61B 17/1703 606/130 |
| 2016/0144510 | A1* | 5/2016 | Gulhar ................ A61B 8/4218 901/4 |
| 2017/0079722 | A1 | 3/2017 | O'Grady et al. |
| 2017/0273748 | A1 | 9/2017 | Hourtash et al. |
| 2017/0333141 | A1 | 11/2017 | Itkowitz et al. |
| 2017/0333142 | A1 | 11/2017 | Itkowitz et al. |
| 2017/0334067 | A1* | 11/2017 | Swarup .................. B25J 19/021 |
| 2018/0280095 | A1 | 10/2018 | Lattimore |
| 2018/0289427 | A1* | 10/2018 | Griffiths ................ A61G 13/04 |

FOREIGN PATENT DOCUMENTS

| | | |
|---|---|---|
| CN | 105832488 A | 8/2016 |
| CN | 107260308 A | 10/2017 |
| CN | 206880734 U | 1/2018 |
| WO | 2017220822 A1 | 12/2017 |

OTHER PUBLICATIONS

International Search Report, Written Opinion, and Claims (Translation) for PCT International App. Serial No. PCT/CN2018/097467; dated Oct. 8, 2018; 9 pages.

Supplementary European Search Report of the European Patent Office, Issued in European Application No. 18915439.6-1113; dated Jan. 4, 2022; 8 pages.

* cited by examiner

METHOD FOR CONTROLLING A MECHANICAL ARM OF A SURGICAL ROBOT FOLLOWING THE MOVEMENT OF A SURGICAL BED AND A DEVICE THEREFOR

CROSS-REFERENCE TO RELATED APPLICATIONS

This application claims the priority benefit of Chinese patent application CN202011150378.1 filed on Oct. 23, 2020, which is incorporated by reference herein in its entirety.

TECHNICAL FIELD

The present application relates to the technical field of medical devices, in particular to a method for controlling a mechanical arm of a surgical robot following the movement of a surgical bed and a device therefor.

BACKGROUND

The Da Vinci Surgical System is an advanced robotic platform the design concept of which is implementing complex minimally invasive surgical operations through the use of a robotic method. The Da Vinci Surgical System is composed of the following three portions: a surgeon console, a bedside mechanical arm system and an imaging system.

The current method for controlling a mechanical arm of a surgical robot needs to disassemble the mechanical arm of the robot and a trocar thereof when adjusting the body posture of a patient, and after the adjusting, the mechanical arm and the trocar are reassembled and reconnected so as to continue operating, which leads to a complicated and time-consuming operation, and an offset for the visual field of a doctor, and meanwhile, the anesthesia time for a patient increases which is likely to bring danger to the patient. With the self-customized bed by Da Vinci, other surgical beds are not compatible and other robotic surgical systems need to disconnect the trocar.

SUMMARY

Regarding above issues, the present application provides a method for controlling a mechanical arm of a surgical robot following the movement of a surgical bed and a device therefor, which solve the technical problems of necessarily disassembling and assembling the mechanical arm of the robot when adjusting the body posture in the related art which results in a complicated and time-consuming operation and is likely to bring danger to a patient. Meanwhile, the method and device of the present application achieve both the compatibility with other beds and non-disconnection of the trocar, and the trocar need not to be removed out of the abdominal cavity during the whole process, which saves time and improves the efficiency of operating, and reduces the possibility of bringing danger to the patient.

In a first aspect, the present application provides a method for controlling a mechanical arm of a surgical robot following the movement of a surgical bed, the method comprises the following steps:

detecting in real time if a change of posture of the surgical bed occurs;

synchronously calculating offsets of a first mechanical arm, a second mechanical arm and an endoscopy mechanical arm corresponding to the change of posture of the surgical bed when the change of posture of the surgical bed is detected, the offsets include target three-dimension coordinates of a trocar remote center of motion (RCM) and a tool tip (TIP) of each of the first mechanical arm, the second mechanical arm and the endoscopy mechanical arm;

calculating target joint readings of each of the first mechanical arm, the second mechanical arm and the endoscopy mechanical arm based on the offsets; and adjusting in real time the first mechanical arm, the second mechanical arm and the endoscopy mechanical arm, based on the calculated target joint readings of each of the first mechanical arm, the second mechanical arm and the endoscopy mechanical arm.

Alternatively, the step of detecting in real time if a change of posture of the surgical bed occurs comprises:

detecting in real time if a change of posture of the surgical bed occurs by means of an optical sensor; and tracking and recording in real time a change of position and posture of an optical sensor by means of an optical tracking camera.

Alternatively, the step of synchronously calculating offsets of a first mechanical arm, a second mechanical arm and an endoscopy mechanical arm corresponding to the change of posture of the surgical bed when the change of posture of the surgical bed is detected comprises:

acquiring three-dimension coordinate offsets of the change of posture of the surgical bed;

calculating target three-dimension coordinates of the trocar remote center of motion (RCM) of each of the first mechanical arm, the second mechanical arm and the endoscopy mechanical arm, based on the three-dimension coordinate offsets of the change of posture of the surgical bed and current three-dimension coordinates of the trocar remote center of motion (RCM) of each of the first mechanical arm, the second mechanical arm and the endoscopy mechanical arm;

calculating current three-dimension coordinates of the tool tip (TIP) of each of the first mechanical arm, the second mechanical arm and the endoscopy mechanical arm with the postures of the mechanical arms kept unchanged, based on current three-dimension coordinates of the trocar remote center of motion (RCM) of each of the first mechanical arm, the second mechanical arm and the endoscopy mechanical arm; and calculating the three-dimension coordinate offsets of the change of posture of the surgical bed and target three-dimension coordinates of the tool tip (TIP) of each of the first mechanical arm, the second mechanical arm and the endoscopy mechanical arm, based on the three-dimension coordinate offsets of the change of posture of the surgical bed and current three-dimension coordinates of the tool tip (TIP) of each of the first mechanical arm, the second mechanical arm and the endoscopy mechanical arm.

Alternatively, the method further comprises:

detecting in real time if the tool tip (TIP) of each of the first mechanical arm, the second mechanical arm and the endoscopy mechanical arm after the adjusting enters into an early warning region adjacent to an operating region; and adjusting in real time the first mechanical arm, the second mechanical arm and/or the endoscopy mechanical arm until it is confirmed that no tool tip (TIP) enters into the early warning region adjacent to the operating region, if at least one tool tip (TIP) entering into the early warning region adjacent to the operating region is detected.

Alternatively, the method further comprises:

detecting in real time if there is a lateral traction force applied to the trocar remote center of motion (RCM) of each of the first mechanical arm, the second mechanical arm and the endoscopy mechanical arm after the adjusting; and adjusting in real time the first mechanical arm, the second mechanical arm and/or the endoscopy mechanical arm until no lateral traction force is detected, if a lateral traction force is detected.

In a second aspect, a device for controlling a mechanical arm of a surgical robot following the movement of a surgical bed, comprising:

a first detecting unit for detecting in real time if a change of posture of the surgical bed occurs;

a first calculating unit for synchronously calculating offsets of a first mechanical arm, a second mechanical arm and an endoscopy mechanical arm corresponding to the change of posture of the surgical bed when the change of posture of the surgical bed is detected, the offsets include target three-dimension coordinates of a trocar remote center of motion (RCM) and a tool tip (TIP) of each of the first mechanical arm, the second mechanical arm and the endoscopy mechanical arm;

a second calculating unit for calculating target joint readings of each of the first mechanical arm, the second mechanical arm and the endoscopy mechanical arm based on the offsets; and an adjusting unit for adjusting in real time the first mechanical arm, the second mechanical arm and the endoscopy mechanical arm, based on the calculated target joint readings of each of the first mechanical arm, the second mechanical arm and the endoscopy mechanical arm.

Alternatively, the first detecting unit is used for detecting in real time if a change of posture of the surgical bed occurs by means of an optical sensor; and tracking and recording in real time a change of position and posture of an optical sensor by means of an optical tracking camera.

Alternatively, the first calculating unit comprises:

an acquiring subunit for acquiring three-dimension coordinate offsets of the change of posture of the surgical bed;

a calculating subunit for:

calculating target three-dimension coordinates of the trocar remote center of motion (RCM) of each of the first mechanical arm, the second mechanical arm and the endoscopy mechanical arm, based on the three-dimension coordinate offsets of the change of posture of the surgical bed and current three-dimension coordinates of the trocar remote center of motion (RCM) of each of the first mechanical arm, the second mechanical arm and the endoscopy mechanical arm;

calculating current three-dimension coordinates of the tool tip (TIP) of each of the first mechanical arm, the second mechanical arm and the endoscopy mechanical arm with the postures of the mechanical arms kept unchanged, based on current three-dimension coordinates of the trocar remote center of motion (RCM) of each of the first mechanical arm, the second mechanical arm and the endoscopy mechanical arm; and calculating the three-dimension coordinate offsets of the change of posture of the surgical bed and target three-dimension coordinates of the tool tip (TIP) of each of the first mechanical arm, the second mechanical arm and the endoscopy mechanical arm, based on the three-dimension coordinate offsets of the change of posture of the surgical bed and current three-dimension coordinates of the tool tip (TIP) of each of the first mechanical arm, the second mechanical arm and the endoscopy mechanical arm.

Alternatively, the device further comprises:

a second detecting unit for detecting in real time if the tool tip (TIP) of each of the first mechanical arm, the second mechanical arm and the endoscopy mechanical arm after the adjusting enters into an early warning region adjacent to an operating region; and wherein the adjusting unit is further used for adjusting in real time the first mechanical arm, the second mechanical arm and/or the endoscopy mechanical arm until it is confirmed that no tool tip (TIP) enters into the early warning region adjacent to the operating region, if at least one tool tip (TIP) entering into the early warning region adjacent to the operating region is detected.

Alternatively, the device further comprises:

a third detecting unit for detecting in real time if there is a lateral traction force applied to the trocar remote center of motion (RCM) of each of the first mechanical arm, the second mechanical arm and the endoscopy mechanical arm after the adjusting; and wherein the adjusting unit is further used for adjusting in real time the first mechanical arm, the second mechanical arm and/or the endoscopy mechanical arm until no lateral traction force is detected, if a lateral traction force is detected.

The present application provides a method for controlling a mechanical arm of a surgical robot following the movement of a surgical bed and a device therefor, by which synchronously calculating offsets of a first mechanical arm, a second mechanical arm and an endoscopy mechanical arm corresponding to a change of posture of the surgical bed when the change of posture of the surgical bed is detected in real time, the offsets include target three-dimension coordinates of a trocar remote center of motion (RCM) and a tool tip (TIP) of each of the first mechanical arm, the second mechanical arm and the endoscopy mechanical arm; calculating target joint readings of each of the first mechanical arm, the second mechanical arm and the endoscopy mechanical arm based on the offsets; adjusting in real time the first mechanical arm, the second mechanical arm and the endoscopy mechanical arm, based on the calculated target joint readings of each of the first mechanical arm, the second mechanical arm and the endoscopy mechanical arm. The present application acquires the joint readings of the mechanical arm of the surgical robot with information about a change of posture of the surgical bed so as to achieve the purpose of synchronizing the mechanical arm with the change of posture of the surgical bed, and meanwhile, achieving that the relative position of the tool tip (TIP) of each of the first mechanical arm, the second mechanical arm and/or the endoscopy mechanical arm keeps constant, and disassembling and assembling the mechanical arm of the surgical robot are not needed when a change of posture of the surgical bed occurs, even removing the trocar out of the abdominal cavity is not required, which saves time and improves the efficiency of operating, and reduces the possibility of bringing danger to the patient.

BRIEF DESCRIPTION OF THE DRAWINGS

Drawings which are necessarily used in the embodiments of the present invention and the prior art are simply explained below so as to more clearly illustrate the technical solutions in the embodiments and the prior art. It is obvious that the drawings descripted below are only the embodiments of the present invention and other drawings may also be acquired by those ordinary skilled in the art based on the drawings provided herein without involving creative labor.

DETAILED DESCRIPTION

The implementations of the present application are explained in detail in combination with the drawings and embodiments, thereby the implementation procedure of how the present application solves the technical problems by applying technical means and achieve corresponding technical effects can be fully understood and implemented. The embodiments and various features thereof of the present application can combine with each other in the condition that there is no confliction therebetween, and the formed technical solutions are also within the protection scope of the present application.

As known from the Background, the current method of controlling a mechanical arm of a surgical robot following the movement of a surgical bed needs to disassemble the mechanical arm of the robot when adjusting the body posture, and after the adjusting, the mechanical arm is reassembled to continue operating, which leads to a complicated and time-consuming operation, and meanwhile, the anesthesia time for a patent increases which is likely to bring danger to the patient.

In view of above, the present application provides a method for controlling a mechanical arm of a surgical robot following the movement of a surgical bed and a device therefor, which solve the technical problems of necessarily disassembling and assembling the mechanical arm of the robot when adjusting the body posture in the related art, which results in complicated and time-consuming operations and is likely to bring danger to a patient.

Embodiment 1

Figure 1:
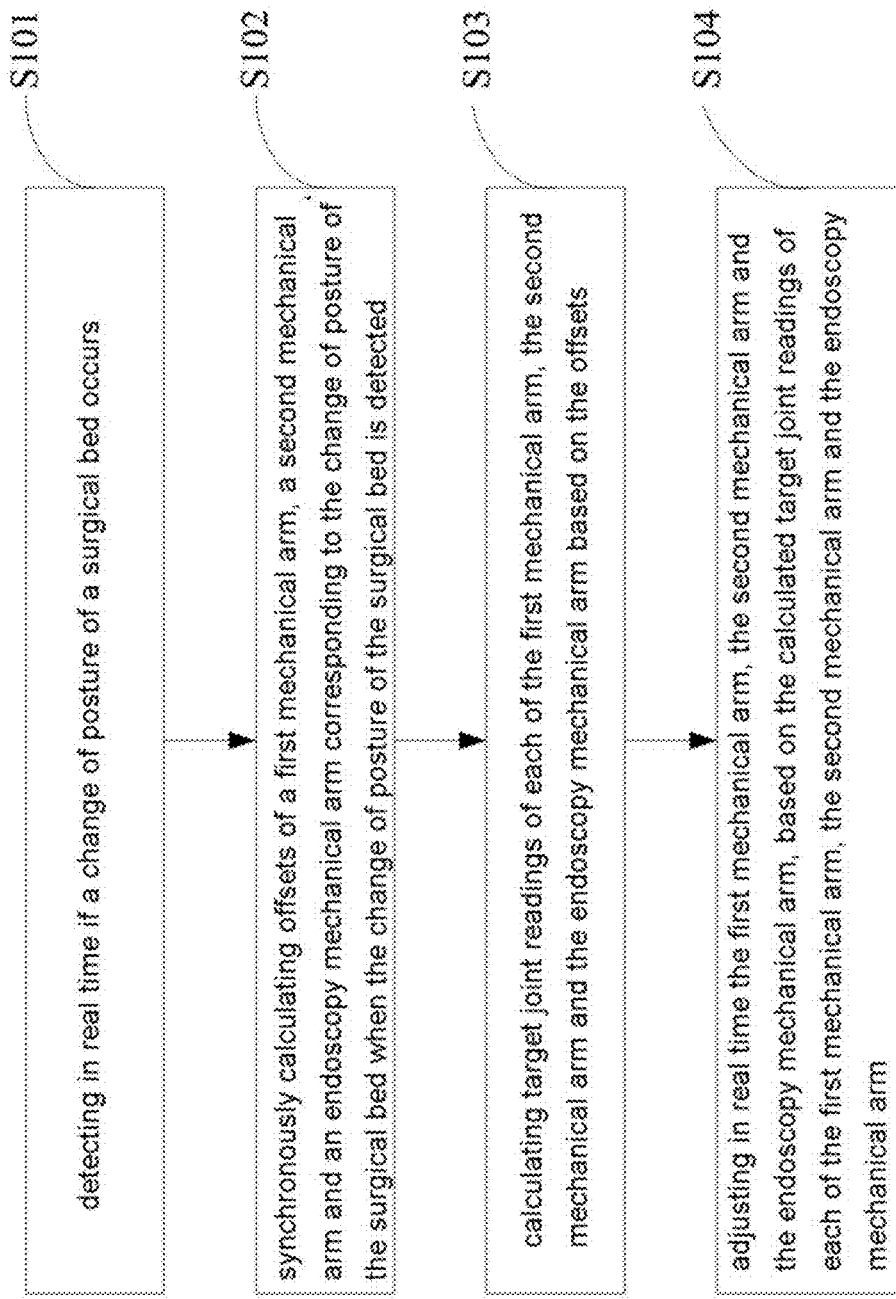
FIG. 1 is a schematic flow diagram of a method for controlling a mechanical arm of a surgical robot following the movement of a surgical bed, according to an embodiment of the present application.

FIG. 1 is a schematic flow diagram of a method for controlling a mechanical arm of a surgical robot following the movement of a surgical bed, according to an embodiment of the present application. As shown in FIG. 1, the method comprises the following steps:

S101: detecting in real time if a change of posture of a surgical bed occurs.

S102: synchronously calculating offsets of a first mechanical arm, a second mechanical arm and an endoscopy mechanical arm corresponding to the change of posture of the surgical bed when the change of posture of the surgical bed is detected.

In the step S102, the offsets include target three-dimension coordinates of a trocar remote center of motion (RCM) and a tool tip (TIP) of each of the first mechanical arm, the second mechanical arm and the endoscopy mechanical arm.

S103: calculating target joint readings of each of the first mechanical arm, the second mechanical arm and the endoscopy mechanical arm based on the offsets.

S104: adjusting in real time the first mechanical arm, the second mechanical arm and the endoscopy mechanical arm, based on the calculated target joint readings of each of the first mechanical arm, the second mechanical arm and the endoscopy mechanical arm.

Specifically, during an operation seen from a doctor's view field, an image of the doctor's view field always align with the operating scope of the operation during the whole process of the following movement of the surgical bed, and the related organs provide a broader operating space for the doctor due to a change of the inclination of the surgical bed occurs.

It needs to illustrate that the surgical bed can change its posture with six degrees of freedom, in which comprising translation in X, Y, Z directions, and pitching, yawing and rolling. Thereby, accomplishing the requirements for robot-assistant operations in Gynecology, Urology, General Surgery, Vascular Surgery and Thoracic Surgery, etc. cooperating with the surgical robot.

It needs to further illustrate that the surgical bed may be an electric surgical bed or a manual surgical bed, it can be applied in the technical solutions of the present application as long as it satisfies the requirements for a change of posture.

Alternatively, the step of detecting in real time if a change of posture of the surgical bed occurs comprises:

detecting in real time if a change of posture of the surgical bed occurs by means of an optical sensor; and tracking and recording in real time a change of position and posture of an optical sensor by means of an optical tracking camera.

It needs to illustrate that an optical sensor is a type of sensor, which carries out a measurement according to the principle of optics, and it also has a plurality of advantages, such as, noncontact and noninvasive measurement, almost undisturbed, transferring at a high speed and remote-measurable and remote-controllable, etc.

In addition, an optical sensor in the embodiment is disposed in lower side of the surgical bed and however, the present application includes but is not limited to the setting of the position where the optical sensor is disposed, other settings are also within the protection scope of the present application as long as they satisfy the following position conditions: the mechanical arm does not shield the optical sensor and can collect a change of posture of the surgical bed accurately.

It needs to further illustrate that an optical tracking camera in the embodiment of the present application is disposed under the surgical bed or beside the surgical bed for tracking and recording in real time a change of position and posture of the optical sensor without impacting by lighting and shielding as well as the movement of the doctor during the surgical operating, and meanwhile, enabling totally noncontact with the human body.

Tracking and recording in real time a change of position and posture of an optical sensor by means of an optical tracking camera, and transmitting the recorded data to a calculating unit, such as a computer, for subsequently synchronously calculating offsets of a first mechanical arm, a second mechanical arm and an endoscopy mechanical arm corresponding to the change of posture of the surgical bed when the change of posture of the surgical bed is detected.

Alternatively, the step of synchronously calculating offsets of a first mechanical arm, a second mechanical arm and an endoscopy mechanical arm corresponding to the change of posture of the surgical bed when the change of posture of the surgical bed is detected comprises:

acquiring three-dimension coordinate offsets of the change of posture of the surgical bed;

calculating target three-dimension coordinates of the trocar remote center of motion (RCM) of each of the first mechanical arm, the second mechanical arm and the endoscopy mechanical arm, based on the three-dimension coordinate offsets of the change of posture of the surgical bed and current three-dimension coordinates of the trocar remote center of motion (RCM) of each of the first mechanical arm, the second mechanical arm and the endoscopy mechanical arm;

calculating current three-dimension coordinates of the tool tip (TIP) of each of the first mechanical arm, the second mechanical arm and the endoscopy mechanical arm with the postures of the mechanical arms kept unchanged, based on current three-dimension coordinates of the trocar remote center of motion (RCM) of each of the first mechanical arm, the second mechanical arm and the endoscopy mechanical arm; and calculating the three-dimension coordinate offsets of the change of posture of the surgical bed and target three-dimension coordinates of the tool tip (TIP) of each of the first mechanical arm, the second mechanical arm and the endoscopy mechanical arm, based on the three-dimension coordinate offsets of the change of posture of the surgical bed and current three-dimension coordinates of the tool tip (TIP) of each of the first mechanical arm, the second mechanical arm and the endoscopy mechanical arm.

Figure 2:
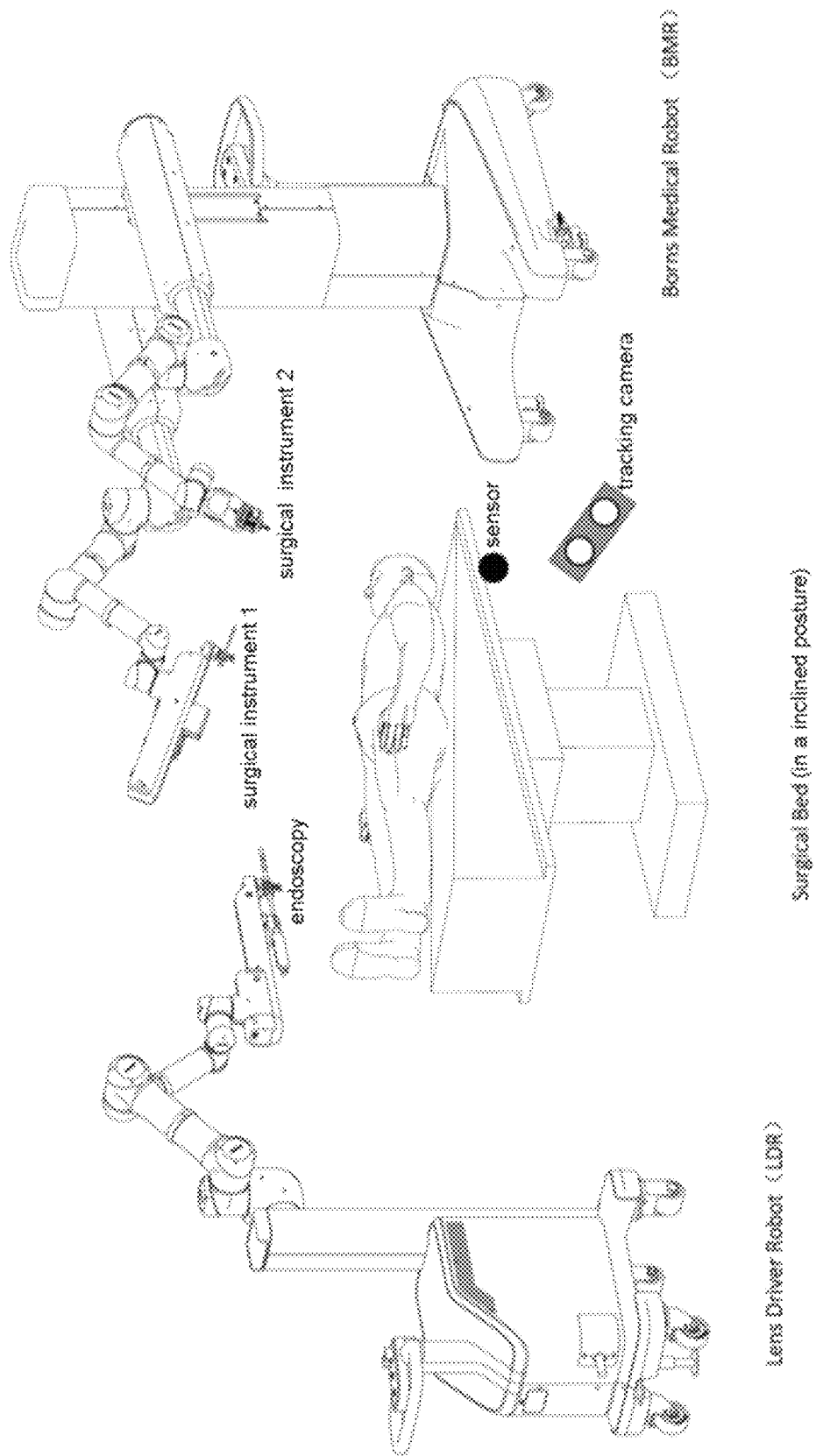
FIG. 2 is a schematic view of an application scenario of a surgical robot and a surgical bed, according to an embodiment of the present application.

It needs to illustrate that, as shown in FIG. 2, which is a schematic view of an application scenario of a surgical robot and a surgical bed disclosed in the present application. As can be seen from FIG. 2, the surgical robot includes two portions: a Lens Driver Robot (LDR) and a Borns Medical Robot (BMR), the original point of the target three-dimension coordinates is the center of the surgical bed, in which the center of the surgical bed refers to the central position of a device for lifting the surgical bed to change its angle, and this central position is also the center of the surgical bed. And in the same three-dimension coordinate system, the relative position between the Lens Driver Robot (LDR) and the Borns Medical Robot (BMR) is determined, and meanwhile, the relative position of the tool tip (TIP) of each of the mechanical arms of the endoscopy keeps constant during the synchronous movement of the mechanical arms of the two Robots with that of the surgical bed.

Specifically, the formats of coordinates of the first mechanical arm, the second mechanical arm and the endoscopy mechanical arm are shown in Table 1 as follows:

TABLE 1

Figure 3:
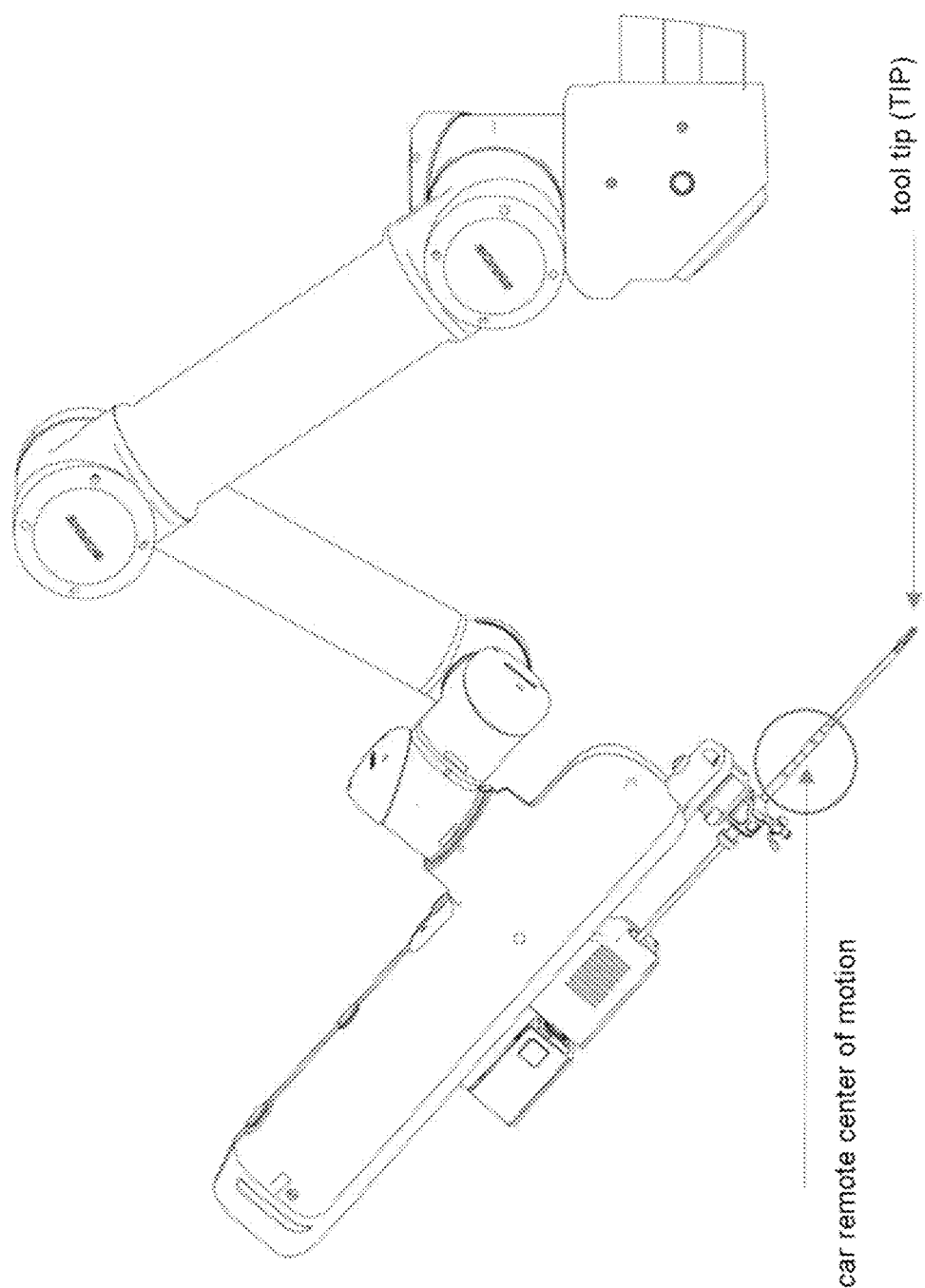
FIG. 3 is a schematic view of positions of a trocar remote center of motion and a tool tip on a mechanical arm, according to an embodiment of the present application.

| Arm No. 1 | Arm No. 2 | Endoscopy arm |
|---|---|---|
| RCM1 (X, Y, Z) | RCM2 (X, Y, Z) | RCM3 (X, Y, Z) |
| TIP1 (X, Y, Z) | TIP2 (X, Y, Z) | TIP3 (X, Y, Z) |

Wherein the positions of a trocar remote center of motion (RCM) and a tool tip (TIP) on a mechanical arm are shown in FIG. 3, in which the RCM is a telecentric fixed point which indicates that enabling the RCM point fixed, i.e., no movement or offset occurs, by a method of controlling (to control a mechanical arm) when the mechanical arm moves.

It needs to illustrate that all of the above detecting, calculating and controlling of the mechanical arms are carried out in real time, ensuring that the movement of the three mechanical arms following that of the surgical bed is connection movement, which can be directly seen as a kind of synchronous movement due to a tiny time difference.

In another embodiment of the present invention, specifically, a Da Vinci Surgical System acts as a surgical robot, which can perfectly connect to a matching electric surgical bed in a wired, wireless or infrared way, enabling linkage among devices; when adjusting the body posture of the surgical bed by changing its angle, the mechanical arm of the robot in linkage also synchronously adjusts its angle without disassembling the mechanical arm so as to avoid hurting other tissues and visceral organs.

Figure 4:
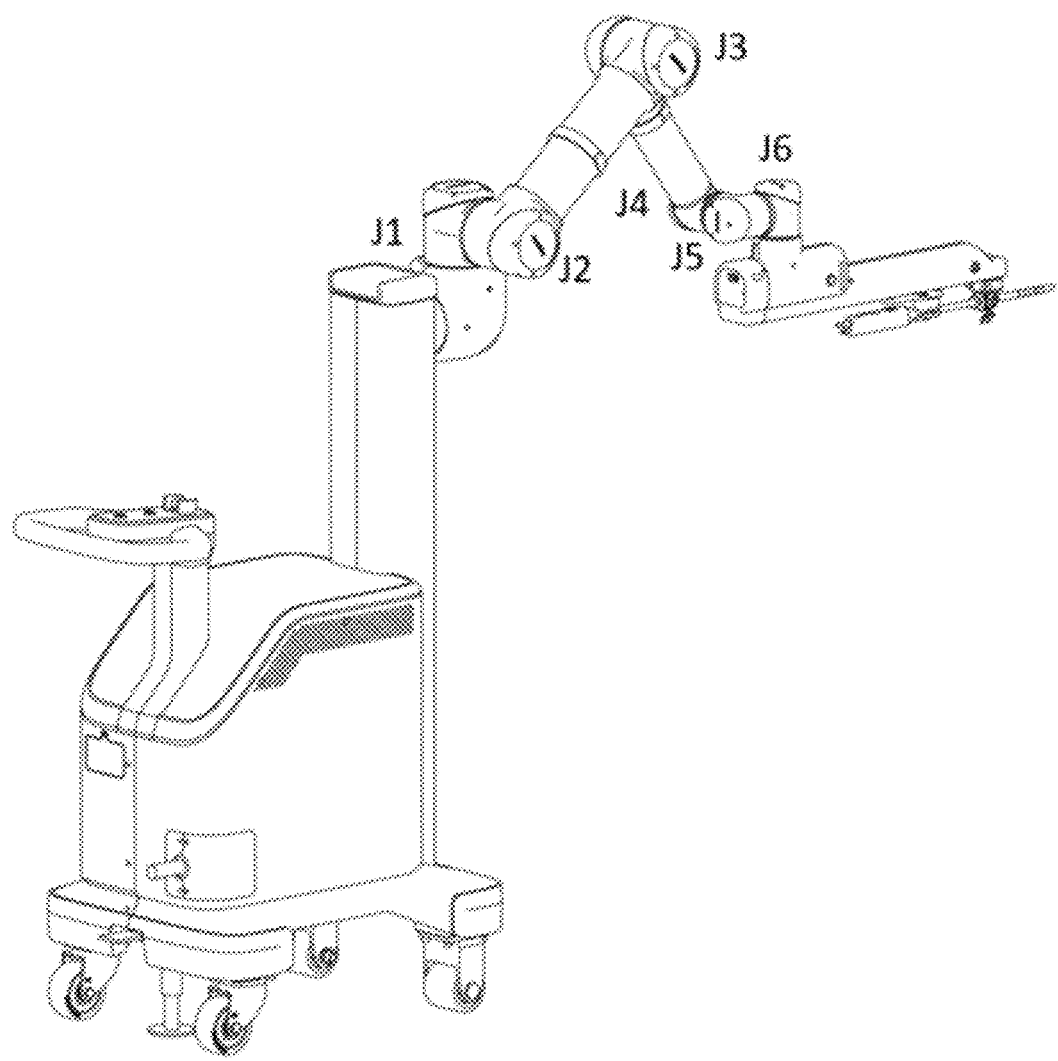
FIG. 4 is a marked graph of joints of a mechanical arm of a Lens Driver Robot, according to an embodiment of the present application.
Figure 5:
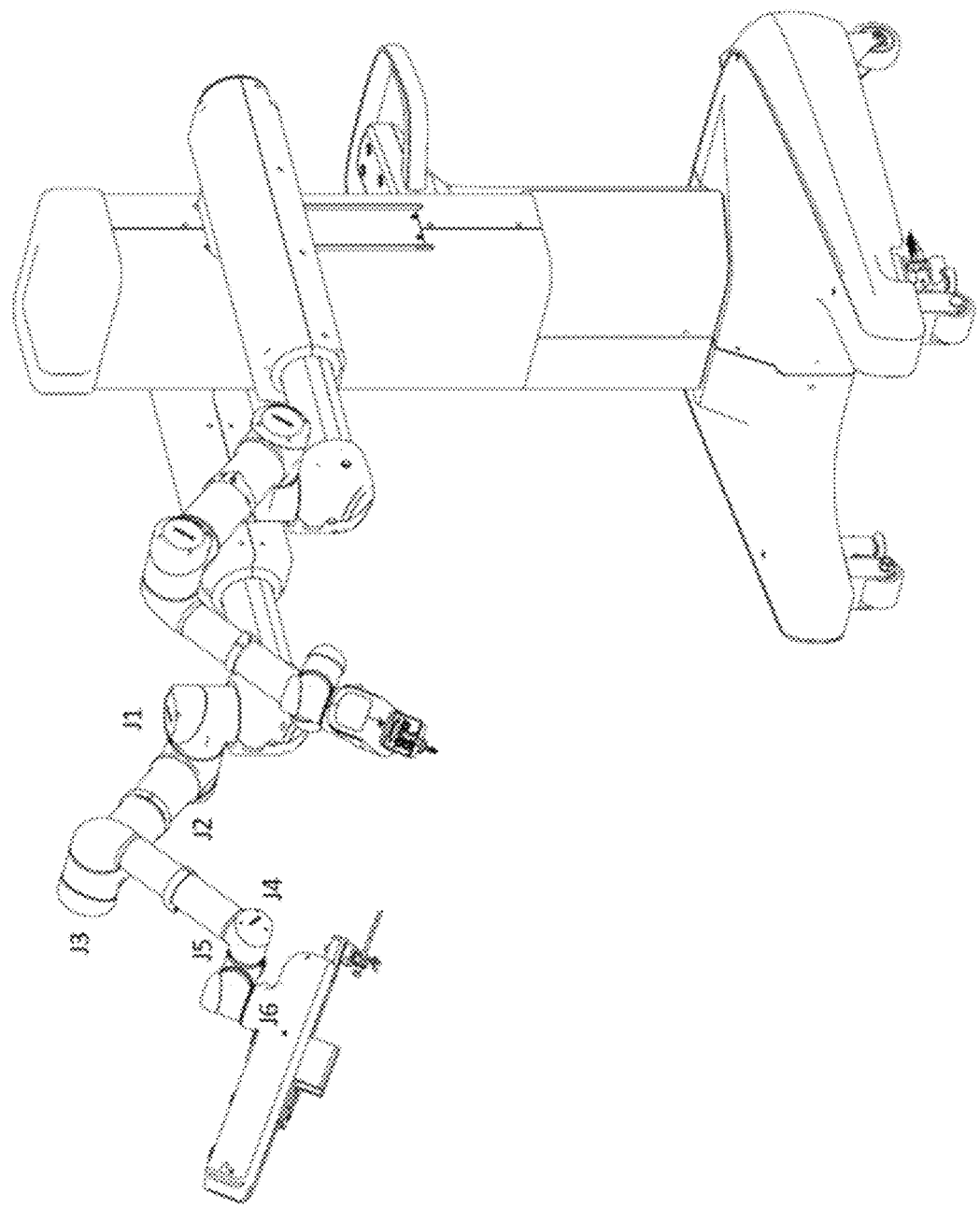
FIG. 5 is a marked graph of joints of a first mechanical arm of a Borns Medical Robot, according to an embodiment of the present application.

It needs to illustrate that the step of calculating target joint readings of each of the first mechanical arm, the second mechanical arm and the endoscopy mechanical arm based on the offsets can be specifically carried out by calculating new joint readings of each of the first mechanical arm, the second mechanical arm and the endoscopy mechanical arm by means of Inverse Kinematics (IK). And as shown in FIG. 4 and FIG. 5, FIG. 4 is a marked graph of joints of a mechanical arm of a Lens Driver Robot, according to an embodiment of the present application, and J1-J6 shown in FIG. 4 are respective joints of the mechanical arm of the Lens Driver Robot; FIG. 5 is a marked graph of joints of a first mechanical arm of a Borns Medical Robot, according to an embodiment of the present application, and J1-J6 shown in FIG. 5 are respective joints of the first mechanical arm of the Borns Medical Robot; it needs to illustrate that a second mechanical arm in FIG. 5 is not marked due to its joints are the same as that of the first mechanical arm in FIG. 5.

Alternatively, the method further comprises:

detecting in real time if the tool tip (TIP) of each of the first mechanical arm, the second mechanical arm and the endoscopy mechanical arm after the adjusting enters into an early warning region adjacent to an operating region; and adjusting in real time the first mechanical arm, the second mechanical arm and/or the endoscopy mechanical arm until it is confirmed that no tool tip (TIP) enters into the early warning region adjacent to the operating region, if at least one tool tip (TIP) entering into the early warning region adjacent to the operating region is detected.

Figure 6:
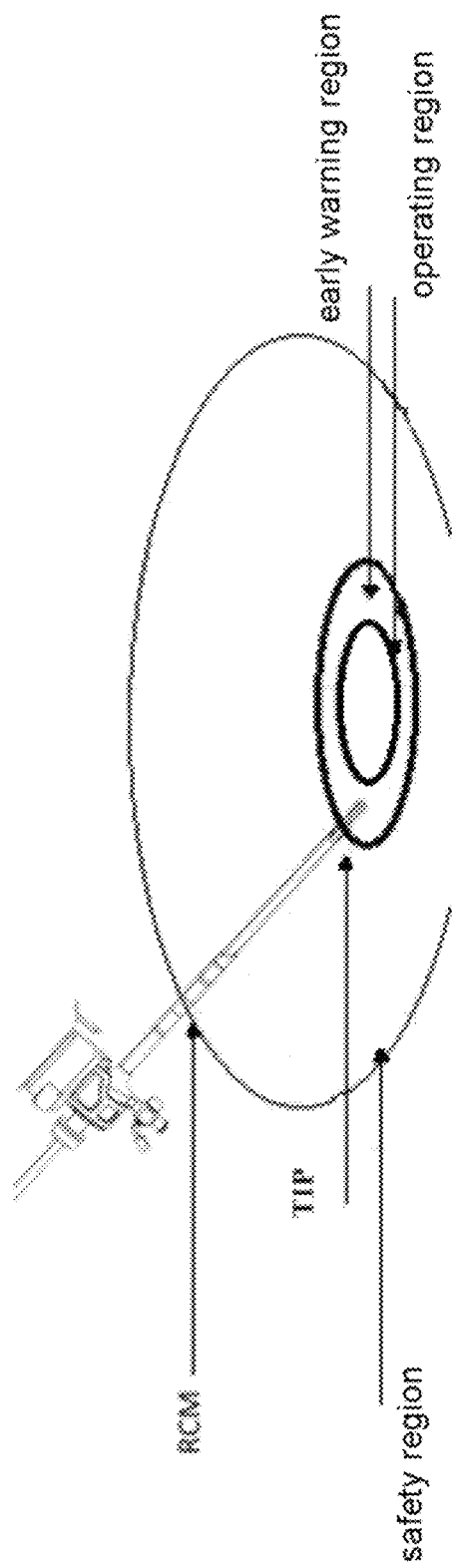
FIG. 6 is a schematic view of a position of an early warning region adjacent to an operating region, according to an embodiment of the present application.

As shown in FIG. 6, it is a schematic view of a position of an early warning region adjacent to an operating region, according an embodiment of the present application.

It needs to illustrate that the position of the tool tip (TIP) is required to be detected in real time to ensure that the tool tip (TIP) is in a safety region which cannot hurt the internal body tissues so as to avoid the tool tip (TIP) of a mechanical arm from contacting internal body tissues, such as viscera organs, during its movement, which results in injury of the internal body tissues. In FIG. 3, a region having a maximum range is the safety region, a region in the inner most circle is the operating region, a region in the middle is the region adjacent to the operating region and a region between the safety region and the operating region is the early warning region.

Alternatively, the method further comprises:

detecting in real time if there is a lateral traction force applied to the trocar remote center of motion (RCM) of each of the first mechanical arm, the second mechanical arm and the endoscopy mechanical arm after the adjusting; and adjusting in real time the first mechanical arm, the second mechanical arm and/or the endoscopy mechanical arm until no lateral traction force applied to the trocar remote center of motion (RCM) is detected, if a lateral traction force is detected.

It needs to illustrate that the lateral traction force at the RCM point is required to be detected to ensure that there is no lateral traction force so as to avoid the trocar remote center of motion (RCM) from generating the lateral traction force during the mechanical arm's movement, which results in injury of body tissues. Specifically, if there is a lateral traction force applied to the trocar remote center of motion (RCM) of each of the first mechanical arm, the second mechanical arm and the endoscopy mechanical arm can be determined by pushing a releasing button on the mechanical arm. By pushing the releasing button on the mechanical arm, the mechanical arm enters into a gravity compensation mode, where the mechanical arm can compensate for the gravity by controlling the torque of a joint to detect if there is a lateral traction force applied to the trocar remote center of motion (RCM).

In conclusion, the embodiments of the present application provide a method for controlling a mechanical arm of a surgical robot following the movement of a surgical bed, the method comprises the following steps: synchronously calculating offsets of a first mechanical arm, a second mechanical arm and an endoscopy mechanical arm corresponding to the change of posture of the surgical bed when the change of posture of the surgical bed is detected in real time, the offsets include target three-dimension coordinates of a trocar remote center of motion (RCM) and a tool tip (TIP) of each of the first mechanical arm, the second mechanical arm and the endoscopy mechanical arm; calculating target joint readings of each of the first mechanical arm, the second mechanical arm and the endoscopy mechanical arm based on the offsets; adjusting in real time the first mechanical arm, the second mechanical arm and the endoscopy mechanical arm, based on the calculated target joint readings of each of the first mechanical arm, the second mechanical arm and the endoscopy mechanical arm. The present application acquires the joint readings of the mechanical arm of the surgical robot with information about a change of posture of the surgical bed so as to achieve the purpose of synchronizing the mechanical arm with the change of posture of the surgical bed, and disassembling and assembling the mechanical arm of the surgical robot are not needed when a change of posture of the surgical bed occurs, even removing the trocar out of the abdominal cavity is not required, which saves time and improves the efficiency of operating, and reduces the possibility of bringing danger to the patient.

Embodiment 2

Figure 7:
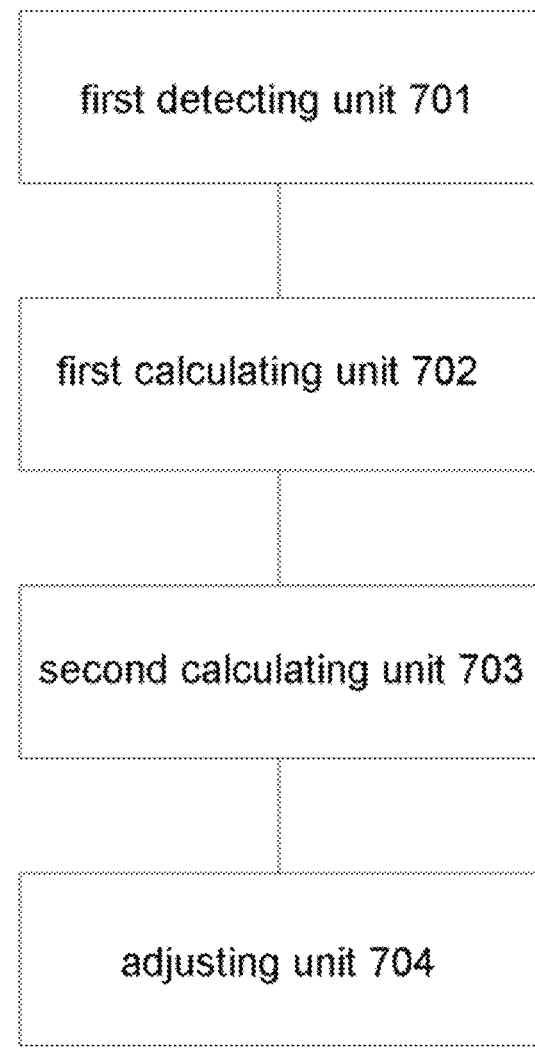
FIG. 7 is a schematic structure of a device for controlling a mechanical arm of a surgical robot following the movement of a surgical bed, according to an embodiment of the present application.

Based on the method for controlling a mechanical arm of a surgical robot following the movement of a surgical bed disclosed in above embodiments of the present invention, FIG. 7 specifically discloses a device for controlling a mechanical arm of a surgical robot following the movement of a surgical bed, which uses the method for controlling a mechanical arm of a surgical robot following the movement of a surgical bed.

As shown in FIG. 7, an embodiment of the present invention discloses a device for controlling a mechanical arm of a surgical robot following the movement of a surgical bed, the device comprises:

a first detecting unit 701 for detecting in real time if a change of posture of the surgical bed occurs;

a first calculating unit 702 for synchronously calculating offsets of a first mechanical arm, a second mechanical arm and an endoscopy mechanical arm corresponding to the change of posture of the surgical bed when the change of posture of the surgical bed is detected, the offsets include target three-dimension coordinates of a trocar remote center of motion (RCM) and a tool tip (TIP) of each of the first mechanical arm, the second mechanical arm and the endoscopy mechanical arm;

a second calculating unit 703 for calculating target joint readings of each of the first mechanical arm, the second mechanical arm and the endoscopy mechanical arm based on the offsets; and an adjusting unit 704 for adjusting in real time the first mechanical arm, the second mechanical arm and the endoscopy mechanical arm, based on the calculated target joint readings of each of the first mechanical arm, the second mechanical arm and the endoscopy mechanical arm.

Alternatively, the first detecting unit 701 is used for detecting in real time if a change of posture of the surgical bed occurs by means of an optical sensor; and tracking and recording in real time a change of position and posture of an optical sensor by means of an optical tracking camera.

Alternatively, the first calculating unit 702 comprises:

an acquiring subunit for acquiring three-dimension coordinate offsets of the change of posture of the surgical bed;

a calculating subunit for:

calculating target three-dimension coordinates of the trocar remote center of motion (RCM) of each of the first mechanical arm, the second mechanical arm and the endoscopy mechanical arm, based on the three-dimension coordinate offsets of the change of posture of the surgical bed and current three-dimension coordinates of the trocar remote center of motion (RCM) of each of the first mechanical arm, the second mechanical arm and the endoscopy mechanical arm;

calculating current three-dimension coordinates of the tool tip (TIP) of each of the first mechanical arm, the second mechanical arm and the endoscopy mechanical arm with the postures of the mechanical arms kept unchanged, based on current three-dimension coordinates of the trocar remote center of motion (RCM) of each of the first mechanical arm, the second mechanical arm and the endoscopy mechanical arm; and calculating the three-dimension coordinate offsets of the change of posture of the surgical bed and target three-dimension coordinates of the tool tip (TIP) of each of the first mechanical arm, the second mechanical arm and the endoscopy mechanical arm, based on the three-dimension coordinate offsets of the change of posture of the surgical bed and current three-dimension coordinates of the tool tip (TIP) of each of the first mechanical arm, the second mechanical arm and the endoscopy mechanical arm.

Alternatively, the device further comprises:

a second detecting unit for detecting in real time if the tool tip (TIP) of each of the first mechanical arm, the second mechanical arm and the endoscopy mechanical arm after the adjusting enters into an early warning region adjacent to an operating region; and wherein the adjusting unit 704 is further used for adjusting in real time the first mechanical arm, the second mechanical arm and/or the endoscopy mechanical arm until it is confirmed that no tool tip (TIP) enters into the early warning region adjacent to the operating region, if at least one tool tip (TIP) entering into the early warning region adjacent to the operating region is detected.

Alternatively, the device further comprises:

a third detecting unit for detecting in real time if there is a lateral traction force applied to the trocar remote center of motion (RCM) of each of the first mechanical arm, the second mechanical arm and the endoscopy mechanical arm after the adjusting; and wherein the adjusting unit 704 is further used for adjusting in real time the first mechanical arm, the second mechanical arm and/or the endoscopy mechanical arm until no lateral traction force is detected, if a lateral traction force is detected.

Regarding the specific operation processes of the first detecting unit 701, the first calculating unit 702, the second calculating unit 703 and the adjusting unit 704 in the device for controlling a mechanical arm of a surgical robot following the movement of a surgical bed disclosed in above embodiments of the present invention, please refer to the corresponding contents in the description of the method for controlling a mechanical arm of a surgical robot following the movement of a surgical bed disclosed in the above embodiments of the present invention, which are not described herein.

In conclusion, the embodiments of the present application provide a device for controlling a mechanical arm of a surgical robot following the movement of a surgical bed, comprising: synchronously calculating offsets of a first mechanical arm, a second mechanical arm and an endoscopy mechanical arm corresponding to the change of posture of the surgical bed when the change of posture of the surgical bed is detected in real time, the offsets include target three-dimension coordinates of a trocar remote center of motion (RCM) and a tool tip (TIP) of each of the first mechanical arm, the second mechanical arm and the endoscopy mechanical arm; calculating target joint readings of each of the first mechanical arm, the second mechanical arm and the endoscopy mechanical arm based on the offsets; adjusting in real time the first mechanical arm, the second mechanical arm and the endoscopy mechanical arm, based on the calculated target joint readings of each of the first mechanical arm, the second mechanical arm and the endoscopy mechanical arm. The present application acquires the joint readings of the mechanical arm of the surgical robot with information about a change of posture of the surgical bed so as to achieve the purpose of synchronizing the mechanical arm with the change of posture of the surgical bed, and disassembling and assembling the mechanical arm of the surgical robot are not needed when a change of posture of the surgical bed occurs, and meanwhile, it achieves both the compatibility with other beds and non-disconnection of the trocar, even removing the trocar out of the abdominal cavity is not required, which saves time and improves the efficiency of operating, and reduces the possibility of bringing danger to the patient.

In summary, the present application provides a method for controlling a mechanical arm of a surgical robot following the movement of a surgical bed and a device therefor, the method comprises the following steps: synchronously calculating offsets of a first mechanical arm, a second mechanical arm and an endoscopy mechanical arm corresponding to the change of posture of the surgical bed when the change of posture of the surgical bed is detected in real time, the offsets include target three-dimension coordinates of a trocar remote center of motion (RCM) and a tool tip (TIP) of each of the first mechanical arm, the second mechanical arm and the endoscopy mechanical arm; calculating target joint readings of each of the first mechanical arm, the second mechanical arm and the endoscopy mechanical arm based on the offsets; adjusting in real time the first mechanical arm, the second mechanical arm and the endoscopy mechanical arm, based on the calculated target joint readings of each of the first mechanical arm, the second mechanical arm and the endoscopy mechanical arm. The present application acquires the joint readings of the mechanical arm of the surgical robot with information about a change of posture of the surgical bed so as to achieve the purpose of synchronizing the mechanical arm with the change of posture of the surgical bed, and disassembling and assembling the mechanical arm of the surgical robot are not needed when a change of posture of the surgical bed occurs, even removing the trocar out of the abdominal cavity is not required, which saves time and improves the efficiency of operating, and reduces the possibility of bringing danger to the patient.

It should be realized from the several embodiments provided in the present application that the disclosed method can also be implemented in other approaches. Above described embodiments for the method are only exemplary.

It should also be noted that the terms "comprising", "including" or any other variation thereof herein are intended to cover non-exclusive inclusion, so that a process, a method, an article or a device including a series of elements not only includes those elements but also includes other elements which are not explicitly listed, or further includes the inherent elements of the process, the method, the article or the device. Without further restrictions, an element defined by the sentence "comprising a . . . " does not exclude the existence of other identical elements in the process, the method, the article or the device including the element.

Although the embodiments disclosed in the present application as described above, the above contents are only the implementations adopted for the convenience of understanding the present application and not intended to limit the present application. Any person skilled in the technical field to which the present application belongs can make any modifications and changes in the form or details of implementations without departing from the spirit and scope disclosed in the present application. However, the scope of patent protection of the present application shall still be subject to the scope defined in the appended Claims.

What is claimed is:

1. A method for controlling a mechanical arm of a surgical robot following the movement of a surgical bed, the method comprising the following steps:

storing three-dimension coordinates defining an operating region proximal to a patient positioned on the surgical bed and an early warning region adjacent to the operating region;

detecting in real time if a change of posture of the surgical bed occurs;

calculating region offsets of the early warning region and the operating region corresponding to the change of posture of the surgical bed when the change of posture of the surgical bed is detected, and updating the early warning region and the operating region based on the region offsets;

synchronously calculating offsets of a first mechanical arm, a second mechanical arm and an endoscopy mechanical arm corresponding to the change of posture of the surgical bed when the change of posture of the surgical bed is detected, the offsets include target three-dimension coordinates of a trocar remote center of motion (RCM) and a tool tip (TIP) of each of the first mechanical arm, the second mechanical arm and the endoscopy mechanical arm;

calculating target joint readings of each of the first mechanical arm, the second mechanical arm and the endoscopy mechanical arm based on the offsets;

adjusting in real time the first mechanical arm, the second mechanical arm and the endoscopy mechanical arm, based on the calculated target joint readings of each of the first mechanical arm, the second mechanical arm and the endoscopy mechanical arm;

detecting in real time if the tool tip (TIP) of any of the first mechanical arm, the second mechanical arm and the endoscopy mechanical arm after the adjusting enters into the early warning region based on the three-dimension coordinates of the early warning region and current three-dimension coordinates of the first mechanical arm, the second mechanical arm and the endoscope mechanical arm; and if at least one tool tip (TIP) entering into the early warning region adjacent to the operating region is detected, adjusting in real time the mechanical arm of the at least one tool tip (TIP) until it is confirmed that no tool tip (TIP) enters into the early warning region adjacent to the operating region.

2. The method according to claim 1, wherein the step of detecting in real time if a change of posture of the surgical bed occurs comprises:

detecting in real time if a change of posture of the surgical bed occurs by means of an optical sensor; and tracking and recording in real time a change of position and posture of an optical sensor by means of an optical tracking camera.

3. The method according to claim 1, wherein the step of synchronously calculating offsets of a first mechanical arm, a second mechanical arm and an endoscopy mechanical arm corresponding to the change of posture of the surgical bed when the change of posture of the surgical bed is detected comprises:

acquiring three-dimension coordinate offsets of the change of posture of the surgical bed;

calculating target three-dimension coordinates of the trocar remote center of motion (RCM) of each of the first mechanical arm, the second mechanical arm and the endoscopy mechanical arm, based on the three-dimension coordinate offsets of the change of posture of the surgical bed and current three-dimension coordinates of the trocar remote center of motion (RCM) of each of the first mechanical arm, the second mechanical arm and the endoscopy mechanical arm;

calculating current three-dimension coordinates of the tool tip (TIP) of each of the first mechanical arm, the second mechanical arm and the endoscopy mechanical arm with the postures of the mechanical arms kept unchanged, based on current three-dimension coordinates of the trocar remote center of motion (RCM) of each of the first mechanical arm, the second mechanical arm and the endoscopy mechanical arm; and calculating the three-dimension coordinate offsets of the change of posture of the surgical bed and target three-dimension coordinates of the tool tip (TIP) of each of the first mechanical arm, the second mechanical arm and the endoscopy mechanical arm, based on the three-dimension coordinate offsets of the change of posture of the surgical bed and current three-dimension coordinates of the tool tip (TIP) of each of the first mechanical arm, the second mechanical arm and the endoscopy mechanical arm.

4. The method according to claim 1, further comprising:

detecting in real time if there is a lateral traction force applied to the trocar remote center of motion (RCM) of each of the first mechanical arm, the second mechanical arm and the endoscopy mechanical arm after the adjusting; and adjusting in real time the first mechanical arm, the second mechanical arm and/or the endoscopy mechanical arm until no lateral traction force is detected, if a lateral traction force is detected.

5. A device for controlling a mechanical arm of a surgical robot following the movement of a surgical bed, the device comprising:

one or more processors configured for detecting in real time if a change of posture of the surgical bed occurs;

one or more processors further configured for synchronously calculating offsets of a first mechanical arm, a second mechanical arm and an endoscopy mechanical arm corresponding to the change of posture of the surgical bed when the change of posture of the surgical bed is detected, the offsets include target three-dimension coordinates of a trocar remote center of motion (RCM) and a tool tip (TIP) of each of the first mechanical arm, the second mechanical arm and the endoscopy mechanical arm;

one or more processors further configured for calculating target joint readings of each of the first mechanical arm, the second mechanical arm and the endoscopy mechanical arm based on the offsets;

one or more processors further configured for adjusting in real time the first mechanical arm, the second mechanical arm and the endoscopy mechanical arm, based on the calculated target joint readings of each of the first mechanical arm, the second mechanical arm and the endoscopy mechanical arm;

one or more processors further configured for detecting in real time if there is a lateral traction force applied to the trocar remote center of motion (RCM) of any of the first mechanical arm, the second mechanical arm and the endoscopy mechanical arm after the adjusting; and one or more processors further configured for, if a lateral traction force is detected for at least one trocar remote center of motion (RCM), adjusting in real time the mechanical arm of the at least one trocar remote center of motion (RCM) until no lateral traction force is detected; and one or more processors further configured for detecting in real time if the tool tip (TIP) of each of the first mechanical arm, the second mechanical arm and the endoscopy mechanical arm after the adjusting enters into an early warning region adjacent to an operating region; and one or more processors further configured for adjusting in real time the first mechanical arm, the second mechanical arm and/or the endoscopy mechanical arm until it is confirmed that no tool tip (TIP) enters into the early warning region adjacent to the operating region, if at least one tool tip (TIP) entering into the early warning region adjacent to the operating region is detected.

6. The device according to claim 5, wherein the one or more processors are further configured to:

detect in real time if a change of posture of the surgical bed occurs by means of an optical sensor; and track and record in real time a change of position and posture of an optical sensor by means of an optical tracking camera.

7. The device according to claim 5, wherein the one or more processors are further configured to:
acquire three-dimension coordinate offsets of the change of posture of the surgical bed;
calculate target three-dimension coordinates of the trocar remote center of motion (RCM) of each of the first mechanical arm, the second mechanical arm and the endoscopy mechanical arm, based on the three-dimension coordinate offsets of the change of posture of the surgical bed and current three-dimension coordinates of the trocar remote center of motion (RCM) of each of the first mechanical arm, the second mechanical arm and the endoscopy mechanical arm;
calculate current three-dimension coordinates of the tool tip (TIP) of each of the first mechanical arm, the second mechanical arm and the endoscopy mechanical arm with the postures of the mechanical arms kept unchanged, based on current three-dimension coordinates of the trocar remote center of motion (RCM) of each of the first mechanical arm, the second mechanical arm and the endoscopy mechanical arm; and
calculate the three-dimension coordinate offsets of the change of posture of the surgical bed and target three-dimension coordinates of the tool tip (TIP) of each of the first mechanical arm, the second mechanical arm and the endoscopy mechanical arm, based on the three-dimension coordinate offsets of the change of posture of the surgical bed and current three-dimension coordinates of the tool tip (TIP) of each of the first mechanical arm, the second mechanical arm and the endoscopy mechanical arm.

8. The device according to claim 5, wherein each of the first mechanical arm, the second mechanical arm, and the endoscopy mechanical arm comprise a joint motor operable by the one or more processors to adjust that mechanical arm, wherein the one or more processors are further configured to:
detect in real time if there is a lateral traction force applied to the trocar remote center of motion (RCM) of any of the first mechanical arm, the second mechanical arm and the endoscopy mechanical arm after the adjusting based upon the torque of the respective joint motors; and
if a lateral traction force is detected for at least one trocar remote center of motion (RCM), operating the mechanical arm of the at least one trocar remote center of motion (RCM) in a gravity compensation mode until no lateral traction force is detected.

9. A device for controlling a mechanical arm of a surgical robot following the movement of a surgical bed, the device comprising:

(a) an optical sensor component configured to be coupled to a position on the underside of the surgical bed;
(b) an optical tracking camera configured to track a change of position and posture of the optical sensor component; and
(c) one or more processors in communication with the optical tracking camera;
wherein the one or more processors are configured to:
(i) receive a set of image data from the optical tracking camera;
(ii) determine the change of position and posture of the optical sensor component based on the set of image data;
(iii) detect in real time a change of posture of the surgical bed based on the change of position and posture of the optical sensor component;
(iv) when the change in posture of the surgical bed is detected, synchronously calculate offsets of a mechanical arm corresponding to the change of posture of the surgical bed, wherein the offsets include target three-dimension coordinates of a trocar remote center of motion (RCM) and a tool tip (TIP) of the mechanical arm;
(v) calculate target joint readings of the mechanical arm based on the offsets;
(vi) operate one or more joint motors of the mechanical arm to adjust the mechanical arm in real time based on the calculated target joint readings.

10. The device according to claim 9, wherein
the optical tracking camera is statically disposed below the underside of the surgical bed such that the optical sensor component is within a field of view of the optical tracking camera.

11. The device according to claim 10, wherein the position to which the optical sensor component is coupled and the static disposition of the optical tracking camera below the surgical bed are configured such that the optical sensor component remains within the field of view of the optical tracking camera throughout a complete range of motion of the surgical bed.

12. The device according to claim 10, wherein the position to which the optical sensor component is coupled and the static disposition of the optical tracking camera below the surgical bed are configured such that the optical tracking camera's field of view of the optical sensor component is not obstructed by any medical equipment or personnel.

13. The device according to claim 9, wherein the mechanical arm comprises at least six joints that are independently movable by the one or more joint motors, wherein the one or more processors are further configured to calculate target joint readings of the at least six joints based on the offsets and using an inverse kinematics function.

* * * * *